United States Patent [19] [11] 4,113,968
Mori et al. [45] Sep. 12, 1978

[54] PROCESS FOR PREPARATION OF SUBSTITUTED CYCLOPROPANE CARBOXYLIC ACIDS AND ESTERS THEREOF AND INTERMEDIATES OF SAID ACIDS AND ESTERS

[75] Inventors: Fumio Mori, Kurashiki; Yoshiaki Omura, Okayama; Takashi Nishida; Kazuo Itoi, both of Kurashiki, all of Japan

[73] Assignee: Kuraray Co., Ltd., Kurashiki, Japan

[21] Appl. No.: 616,998

[22] Filed: Sep. 26, 1975

[30] Foreign Application Priority Data

| Oct. 3, 1974 | [JP] | Japan | 49-114116 |
| Oct. 3, 1974 | [JP] | Japan | 49-114117 |
| Dec. 28, 1974 | [JP] | Japan | 50-2066 |
| Dec. 28, 1974 | [JP] | Japan | 50-2067 |
| Feb. 27, 1975 | [JP] | Japan | 50-24239 |
| May 23, 1975 | [JP] | Japan | 50-61558 |
| May 30, 1975 | [JP] | Japan | 50-64962 |
| May 30, 1975 | [JP] | Japan | 50-64963 |
| May 30, 1975 | [JP] | Japan | 50-64964 |
| Jun. 30, 1975 | [JP] | Japan | 50-80600 |
| Aug. 28, 1975 | [JP] | Japan | 50-104224 |

[51] Int. Cl.$^2$ ............................................. C07C 67/30
[52] U.S. Cl. ............................... 560/124; 260/326 A;
 260/326 S; 260/327 TH; 260/332.2 R;
 260/347.4; 568/843; 560/104; 560/128;
 560/226; 560/228; 568/845; 568/849; 568/812;
 568/821; 568/826; 568/828; 568/838; 568/839
[58] Field of Search ............... 260/468 H, 486 H, 633,
 260/634; 560/124

[56] References Cited

U.S. PATENT DOCUMENTS

| 3,077,496 | 2/1963 | Julia | 260/468 H |
| 3,354,196 | 11/1967 | Julia | 260/468 H |
| 3,652,652 | 3/1972 | Julia | 260/468 H |
| 3,658,879 | 4/1972 | Julia | 260/468 H |
| 3,666,789 | 5/1972 | Itaya | 260/468 H |
| 3,758,504 | 9/1973 | Matsui | 260/468 H |
| 3,907,718 | 9/1975 | Hall | 260/486 R |

FOREIGN PATENT DOCUMENTS 2,326,077  1/1974  Fed. Rep. of Germany ...... 260/468 H

OTHER PUBLICATIONS

Durand–Dran, Annales de Chemie, pp. 43–45, 58–62 & 69–72.
Hill, J. Org. Chem., 37, pp. 3737–3740 (1972).
House, "Modern Synthetic Reactions," 2nd Ed., pp. 582–586 (1972).
House, J. Org. Chem., 40, pp. 86–92 (1975).
Johnson, J. Amer. Chem. Soc. 92, pp. 741–743 (1970).
Colonge, Chem. Abst. 49:12382a (1955).
Normant, Chem. Abst. 51:5691g (1957).
Colonge, Chem. Abst. 51:10417h (1957).
Colonge, Chem. Abst. 51:12851h (1957).

Primary Examiner—James O. Thomas, Jr.
Assistant Examiner—Michael Shippen
Attorney, Agent, or Firm—Bacon & Thomas

[57] ABSTRACT

When 1-halogeno-3-alkene-2-ol is reacted with an ortho-carboxylic ester and/or a ketene acetal, a γ-halogeno-δ-unsaturated-carboxylic ester is obtained as a main reaction product. When this intermediate is treated with a basic substance, a substituted cyclopropane-carboxylic ester is formed. This ester can be used as an insecticide or an agricultural chemical as it is or after the alcohol residue of the ester has been converted to other alcohol residue.

15 Claims, No Drawings

PROCESS FOR PREPARATION OF SUBSTITUTED CYCLOPROPANE CARBOXYLIC ACIDS AND ESTERS THEREOF AND INTERMEDIATES OF SAID ACIDS AND ESTERS

BACKGROUND OF THE INVENTION (1) Field of the Invention:

This invention relates to a novel process for the synthesis of substituted cyclopropane-carboxylic esters represented by the following general formula

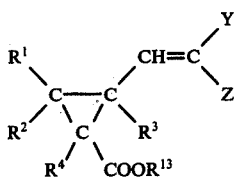
[I]

wherein $R^1$, $R^2$, $R^3$ and $R^4$, which may be the same or different, each stand for hydrogen atom or a hydrocarbon group, $R^1$ and $R^2$ or $R_1$ and $R^3$ may be bonded to form a ring together with the carbon atoms to which they are linked, $R^{13}$ stands for an alcohol residue, and Y and Z, which may be the same or different, each stand for hydrogen or a halogen atom, and to novel intermediates leading to these esters.

Substituted cyclopropane-carboxylic esters represented by general formula [I] are valuable as insecticides or intermediates for synthesis of insecticides. Especially, allethronyl, pyrethronyl, 3-phenoxybenzyl and 5-benzyl-3-furylmethyl esters of 2,2-dimethyl-3-(2',2'-dihalogenovinyl)cyclopropane-carboxylic acids have an insecticidal activity at least several times as high as the insecticidal activity of corresponding esters of chrysanthemic acid and have a highly improved photostability, and these esters are included in pyrethrin analogues which have recently attracted attention in the art as insecticides [see European Chemical News, November 23, 39 (1973); M. Elliot et al, "Nature", 244, 456 (1973); and D. G. Brawn et al, J. Agr. Food Chem., 21, No. 5, 767 (1973)].

(2) Description of the Prior Art: Patent

It is known in the art that the foregoing esters can be prepared by decomposing a lower alkyl ester of chrysanthemic acid with ozone and subjecting the resulting lower alkyl ester of 3-formyl-2,2-dimethyl-cyclopropane-carboxylic acid to the Wittig reaction (see Japanese patent Application Laid-Open Specification No. 47531/74).

This known process, however, is not industrially advantageous, because the starting lower alkyl ester of chrysanthemic acid is expensive and an expensive phosphorus compound should be used as a reactant.

As a result of our research works made with a view to developing a process for preparing the above esters of 2,2-dimethyl-3-(2',2'-dihalogenovinyl)cyclopropane-carboxylic acids at low costs with industrial advantages, we have now found a process in which the Wittig reaction is not utilized.

SUMMARY OF THE INVENTION

In accordance with this invention, there is provided a process for the preparation of substituted cyclopropane-carboxylic esters represented by the following general formula

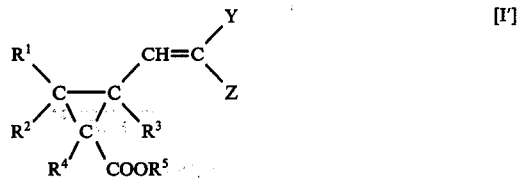
[I']

wherein $R^1$, $R^2$, $R^3$, $R^4$, Y and Z are as defined above in formula [I], and $R^5$ stands for an alcohol residue, which comprises (i) reacting an allyl type alcohol represented by the following general formula

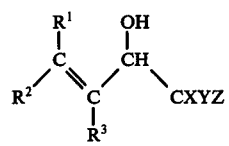
[II]

wherein $R^1$, $R^2$, $R^3$, Y and Z are as defined above, and X is a halogen atom selected from F, Cl, Br and I, with (a) an ortho-carboxylic ester represented by the following general formula

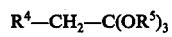
$R^4$—$CH_2$—$C(OR^5)_3$ [III]

wherein $R^4$ and $R^5$ are as defined above, and three of the group $R^5$ may be the same or different, in the presence or absence of an acid catalyst or (b) a ketene acetal represented by the following general formula

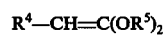
$R^4$—$CH$=$C(OR^5)_2$ [IV]

wherein $R^4$ and $R^5$ are as defined above, and two of the group $R^5$ may be the same or different, and (ii) treating the resulting intermediate with a basic substance.

The so prepared substituted cyclopropane-carboxylic ester of above formula [I'] may be converted, according to need, to a substituted cyclopropane-carboxylic ester of above formula [I] by (iii) converting the alcohol residue $R^5$ of above formula [I'] to other alcohol residue.

Detailed Description of the Invention:

As illustrated hereinbefore, the process of this invention comprises the above steps (i) and (ii) and it further comprises the above step (iii) according to need. These steps (i), (ii) and (iii) will now be described.

(i) Reaction of 1-Halogeno-3-Alkene-2-ol with Ortho-Carboxylic Ester and/or Ketene Acetal It is construed that at this step the reaction proceeds as follows:

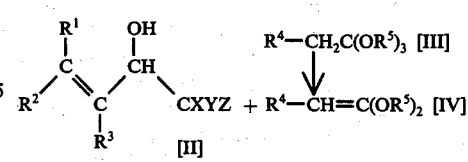

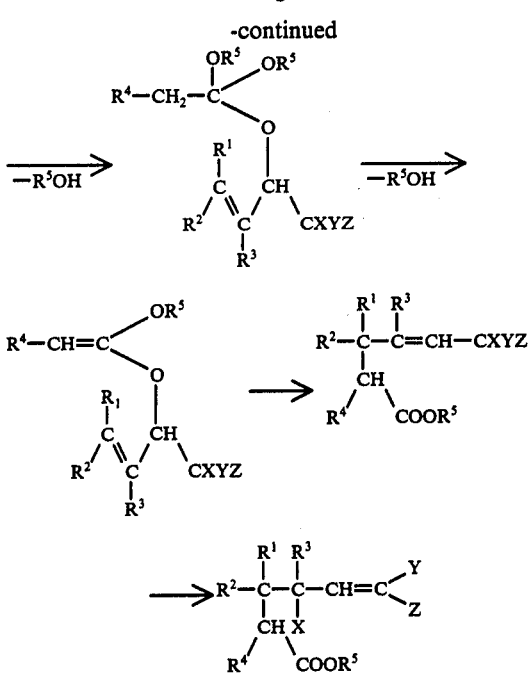

In this reaction various by-products are formed, but from various physical values described below, it is construed that the main reaction product, namely the intermediate of this invention, is a compound represented by the following general formula [V]:

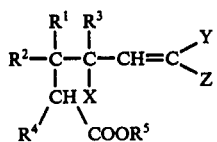 [V]

wherein $R^1$, $R^2$, $R^3$, $R^4$, $R^5$, X, Y and Z are as defined above.

In the 1-halogeno-3-alkene-2-ol represented by above general formula [II], $R^1$, $R^2$ and $R^3$, which may be the same or different, each stand for a hydrogen atom, an alkyl group having up to 15 carbon atoms, a cycloalkyl group having up to 8 carbon atoms, an alkenyl group having up to 15 carbon atoms, a cycloalkenyl group having up to 8 carbon atoms, an alkynyl group having up to 15 carbon atoms, an aryl group having up to 8 carbon atoms or an aralkyl group having up to 10 carbon atoms, and $R^1$ and $R^2$ or $R^1$ and $R^3$ may be bonded to form a ring together with the carbon atoms to which they are linked. X stands for a halogen atom selected from F, Cl, Br and I, and Y and Z stand for a hydrogen or halogen atom.

As typical instances of the 1-halogeno-3-alkene-2-ol represented by general formula [II], there can be mentioned 1,1,1-trichloro-4-methyl-3-penten-2-ol, 1,1,1-tribromo-4-methyl-3-penten-2-ol, 1-chloro-1,1-dibromo-4-methyl-3-penten-2-ol, 1-bromo-1,1dichloro-4-methyl-3-penten-2-ol, 1,1-dichloro-4-methyl-3-penten-2-ol, 1,1-dibromo-4-methyl-3-penten-2-ol, 1,1,1-trichloro-4-methyl-3-hepten-2-ol, 1,1,1-tribromo-4-methyl-3-hepten-2-ol, 1,1-dichloro-4-methyl-3-hepten-2-ol, 1,1-dibromo-4-methyl-3-hepten-2-ol, 1,1,1-trichloro-4,6,6-trimethyl-3-hepten-2-ol, 1,1,1-tribromo-4,6,6-trimethyl-3-heptene-2-ol, 1,1,1-trichloro-4-ethyl-3-hexene-2-ol, 1,1,1-tribromo-4-ethyl-3-hexene-2-ol, 1,1,1-trichloro-4-methyl-3-hexene-2-ol, 1,1,1-tribromo-4-methyl-3-hexene-2-ol, 1,1,1-trichloro-3-heptene-2-ol and 1,1,1-tribromo-3-heptene-2-ol.

Among the foregoing 1-halogeno-3-alkene-2-ol, 1,1,1-trichloro-4-methyl-3-penten-2-ol is a known compound, and this compound can be synthesized, for example, according to a method represented by the following reaction formula [see J. Chem. Soc., (c) 1966, 670]:

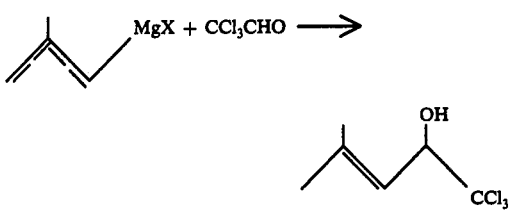

wherein X stands for Cl or Br and

stands for a group

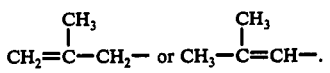

Other 1-halogeno-3-alkene-2-ol are novel compounds, and in general, they can be prepared according to a method represented by the following reaction formula:

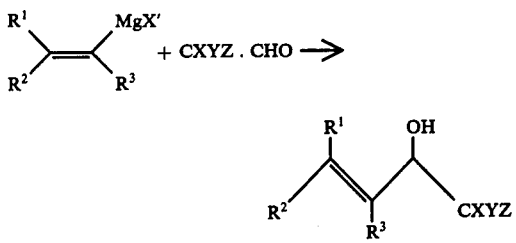

wherein $R^1$, $R^2$, $R^3$, Y and Z are as defined above in general formula [I], and X and X' stand for a halogen atom.

The above process for synthesizing 1-halogeno-3-alkene-2-ol by using Grignard reagents as starting substances involves industrial problems, and it is preferred that 1-halogeno-3-alkene-2-ol be prepared by the following process developed by us:

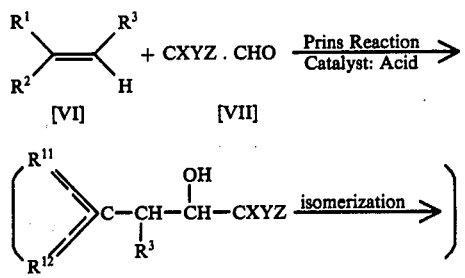

-continued

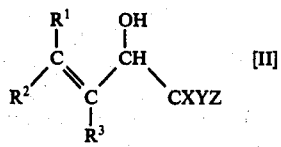

wherein $R^1$, $R^2$, $R^3$, X, Y and Z are as defined above.

In the unsaturated hydrocarbon of general formula [VI] to be used for this synthesis reaction, at least one of $R^1$ and $R^2$ has at least one active hydrogen atom bonded to the carbon atom at the α-position (the carbon atom bonded directly to the double bond).

In the compound represented by the following formula

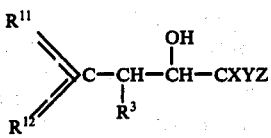

$R^{11}$ is a group which has lost one active hydrogen atom bonded to the carbon atom at the α-position of $R^1$ when $R^{12}$ is the same group as $R^2$ of general formula [VI], and $R^{11}$ is the same group as $R^1$ when $R^{12}$ is a group which has lost one active hydrogen atom bonded to the carbon atom at the α-position of $R^{12}$.

As is seen from the above illustration, the 1-halogeno-3-alkene-2-ol of formula [II] is prepared by subjecting an unsaturated hydrocarbon of formula [VI] and a halogenoacetaldehyde of formula [VII] to the Prins reaction and, according to need, isomerizing the double bond in the resulting reaction product.

As the unsaturated hydrocarbon [VI], there can be mentioned, for example, propene, isobutene, 2-methyl-1-butene diisobutene, 1-pentene, 2-ethyl-1-butene and 2-methyl-1-pentene.

As the halogenoacetaldehyde [VII], there can be mentioned, for example, trichloroacetaldehyde (chloral), tribromoacetaldehyde (bromal), dichloroacetaldehyde, dibromoacetaldehyde, monochloroacetaldehyde, dichlorobromoacetaldehyde and dibromochloroacetaldehyde.

As the acid catalyst to be used for the reaction (the Prins reaction) between the unsaturated hydrocarbon [VI] and the halogenoacetaldehyde [VII], there can be mentioned, for example, Lewis acids such as aluminum chloride, aluminum bromide, boron trifluoroide-diethyl ether, zinc chloride, ferric chloride, tin tetrachloride, tin dichloride, tin tetrabromide, titanium tetrachloride, thallium trichloride, bismuth trichloride, tellurium tetrachloride, tellurium dichloride, antimony pentachloride and phosphorus pentoxide; inorganic acids such as hydrochloric acid, sulfuric acid and phosphoric acid, sulfonic acids such as benzenesulfonic acid, o-toluenesulfonic acid, m-toluenesulfonic acid and p-toluenesulfonic acid, and sulfonyl or carbonyl group-containing ion exchange resins. Among these acid catalysts, aluminum chloride, aluminum bromide, zinc chloride, tin tetrachloride, boron trifluoride-diethyl ether, sulfuric acid and phosphoric acid are preferred.

The amount used of the acid catalyst is varied depending on the kind of the catalyst actually employed, but in general, the acid catalyst is used in an amount of about 0.5 to about 30 mole %, preferably about 3 to about 15 mole %, based on the halogenoacetaldehyde [VII].

The amount used of the unsaturated hydrocarbon [VI] can be changed within a relatively broad range of from about 0.5 to about 6 moles per mole of the halogenoacetaldehyde [VII], but in order to consume the halogenoacetaldehyde [VII] effectively for the reaction, it is preferred to use the unsaturated hydrocarbon [VI] in an amount of 1.0 to 4 mole per mole of the halogenoacetaldehyde [VII].

The reaction is generally carried out at a temperature ranging from −20° C. to room temperature under atmospheric pressure, but if desired, the reaction may be carried out under pressure at a temperature higher than room temperature.

Use of a solvent is not particularly critical in this reaction, but it is possible to employ a solvent not participating in the reaction, for example, petroleum ether, n-pentane, n-hexane and nitromethane.

In many cases, this Prins reaction provides a 1-halogeno-4-alkene-2-ol as the main reaction product. In such cases, this unsaturated alcohol should be converted to a 1-halogeno-3-alkene-2-ol by isomerization of the double bond. This isomerization can be accomplished by the heat treatment in the presence or absence of a catalyst.

As the isomerization catalyst, at least one substance selected from the group consisting of transition metals of the groups VI-B, VII-B and VIII of the Periodic Table and compounds of these transition metals is used.

Preferred isomerization catalysts include chromium [VII] acetylacetonate, molybdenum disulfide, tungsten trioxide, manganese [III] acetylacetonate, ruthenium trichloride, cobalt [II] acetylacetonate, hexamminecobalt chloride, rhodium [III] acetylacetonate, rhodium trichloride, iridium trichloride, Raney-nickel, nickel [II] acetylacetonate, palladium chloride, palladium black, 5% palladium/carbon, and the like.

Further, benzenesulfonic acid, o-, m- p-toluenesulfonic acid and a sulfonyl group-containing ion exchange resin such as Amberlist can be used as the isomerization catalyst.

The isomerization can be performed at a temperature ranging from 60° to 250° C., though the reaction temperature is varied to some extent depending on the kind of the starting 1-halogeno-4-alkene-2-ol. When the isomerization catalyst is employed, the isomerization temperature can be lowered, and the isomerization rate can be enhanced by the presence of the isomerization catalyst if compared based on the same isomerization temperature.

The catalyst is used in an amount of 0.001 to 30% by weight, preferably 0.1 to 10% by weight, based on the 1-halogeno-4-alkene-2-ol.

This isomerization reaction can be conducted either continuously or batchwise. In order to advance the isomerization with a good selectivity, it is preferred that the purity of the starting 1-halogeno-4-alkene-2-ol be heightened and the reaction be carried out in an atmosphere of nitrogen or other inert gas.

The 1-halogeno-3-alkene-2-ol, obtained by the isomerization reaction described above, may be used as one of the starting material between said alcohol and an ortho carboxylic ester or a ketene acetal. In the case, said 1-halogeno-3-alkene-2-ol may be available to use for the reaction, by isolating and purifying it from the liquid reaction mixture obtained by the isomerization reaction, or by using directly said liquid reaction mixture at it is, without isolating and purifying it. Particularly, γ-halogeno-δ-unsaturated carboxylic ester having the formula [V], may be obtained in good yield by using the liquid reaction mixture of the isomerization reaction, which was promoted by using sulfonic acids as the catalyst, directly to the reaction of said reaction mixture and an ortho carboxylic ester or a ketene acetal.

(a) Reaction between 1-Halogeno-3-Alkene-2-Ol and Ortho-carboxylic Ester:

The ortho-carboxylic ester represented by above general formula [III] includes a great number of compounds. In view of easiness in preparation, availability, handling easiness and utility of the intermediate of above formula [V] formed by the reaction (i), it is desirable to use an ortho-carboxylic ester of above formula [VIII] having the following structure:

$R^4$ is a member selected from a hydrogen atom, alkyl groups having up to 15 carbon atoms, cycloalkyl groups having up to 8 carbon atoms, alkenyl groups having up to 15 carbon atoms, cycloalkenyl groups having up to 8 carbon atoms, alkynyl groups having up to 15 carbon atoms, aryl groups having up to 8 carbon atoms and aralkyl groups having up to 10 carbon atoms. Especially preferred examples of $R^4$ are a hydrogen atom, a methyl group, an ethyl group, a propyl group, a butyl group, a cyclohexyl group, a phenyl group and a benzyl group.

Three of alcohol residues $R^5$ (residues formed by removing a hydroxyl group from an alcohol) may be the same or different. As the residue $R^5$, there can be mentioned, for example, alkyl groups having up to 15 carbon atoms, cycloalkyl groups having up to 8 carbon atoms, alkenyl groups having up to 15 carbon atoms, cycloalkenyl groups having up to 8 carbon atoms, and hydrocarbon groups containing a hetero atom such as nitrogen, phosphorus, sulfur or oxygen or a halogen atom.

As such hydrocarbon group, there can be mentioned, for example, hydrocarbon groups represented by the following formula:

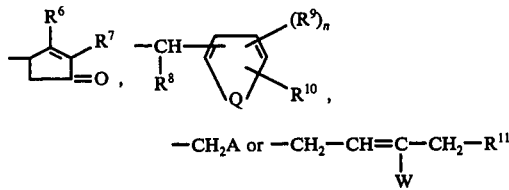

$-CH_2A$ or $-CH_2-CH=C-CH_2-R^{11}$
                              |
                              W wherein $R^6$ stands for a hydrogen atom or a methyl group, $R^7$ stands for an alkenyl, alkadienyl or alkynyl group having up to 6 carbon atoms or a benzyl group, $R^8$ stands for a hydrogen atom, an ethynyl group or a cyano group, $R^9$ stands for a hydrogen atom, a halogen atom or an alkyl group having up to 5 carbon atoms, $R^{10}$ stands for a halogen atom, an alkyl, alkenyl or alkynyl group having up to 6 carbon atoms, or a benzyl, thenyl, furylmethyl, phenoxy or phenylthio group, $R^9$ and $R^{10}$ may be bonded to each other at their terminal ends to form a polymethylene chain in which an oxygen or sulfur atom may be contained, Q stands for an oxygen or sulfur atom or a group $-CH=CH-$, $n$ is an integer or 1 or 2, A stands for a o-, m- or p-phenoxyphenyl group a phthalimido group, a thiophthalimido group, a di- or tetra-hydrophthalimido group or a dialkylmaleimido group, $R^{11}$ stands for a phenyl group, a thienyl group or a furyl group, and W stands for a hydrogen atom, a methyl group, an alkoxy group, a cyano group or a halogen atom.

As preferred examples of the group $R^5$ of the ortho-carboxylic ester of above formula [III], there can be mentioned a methyl group, an ethyl group, a propyl group, a butyl group, an octyl group, a cyclohexyl group, a benzyl group, a prenyl group, a geranyl group, an allethronyl group, a pyrethronyl group, a 3-phenoxybenzyl group, a 5-benzyl-3-furylmethyl group, a tetrahydrophthalimidomethyl group and a 3-benzylpropargyl group.

As preferred examples of the ortho-carboxylic ester of formula [III], there can be mentioned 1,1,1-trimethoxyethane (methyl ortho-acetate), 1,1,1-triethoxyethane (ethyl ortho-acetate), 1,1,1-tricyclohexyloxyethane, 1,1,1-tri-n-butyloxyethane, 1,1,1-triethoxypropane (ethyl ortho-propionate), 1,1,1-triethoxybutane, 1,1,1-triethoxypentane, 3-methyl-1,1,1-triethoxybutane, 3,7-dimethyl-1,1,1-triethoxyoctane, 2-phenyl-1,1,1-triethoxyethane, 2-(o-methylphenyl)-1,1,1-triethoxyethane, 2-(m-methylphenyl)-1,1,1-triethoxyethane, 2-cyclohexyl-1,1,1-trimethoxyethane, 1,1-dimethoxy-1-cyclohexyloxyethane, 1,1-dimethoxy-1-pentoxyethane, 3-methyl-1,1,1-triethoxybutene, 1,1,-triethoxy-6-heptine, 1-benzyloxy-1,1-diethoxyethane, 1,1,-diethoxy-1-geranyloxyethane, 1,1,1-tribenzyloxyethane, 1,1,1-trioctyloxyethane, 1,1-diethoxy-1-octyloxyethane, 1,1-diethoxy-1-prenyloxyethane, 1,1-diethoxy-1-allethronyloxyethane, 1,1-diethoxy-1-pyrethronyloxyethane, 1,1-diethoxy-1-(3-phenoxybenzyloxy)-ethane, 1,1-diethoxy-1-(5-benzyl-3-furylmethoxy)ethane, 1,1-diethoxy-1-(tetrahydrophthalimidomethyloxy)ethane and 1,1-diethoxy-1-(3-benzylpropargyloxy)ethane.

In the reaction (a) between the ortho-carboxylic ester of formula [III] and the 1-halogeno-3-alkene-2-ol [II], the presence of an acid catalyst is not particularly critical, but use of an acid catalyst can promote the speed of the reaction (a).

As the acid catalyst to be used for the reaction (a), there can be mentioned, for example, lower fatty acids such as acetic acid, propionic acid, butyric acid, isobutyric acid, cyclohexylcarboxylic acid, valeric acid, malonic acid, succinic acid and adipic acid; aromatic carboxylic acids such as benzoic acid and m-chlorobenzoic acid, phenols such as phenol, o-nitrophenol, m-nitrophenol, p-nitrophenol, o-cresol, m-cresol, p-cresol, o-xylenol, p-xylenol, 2,6-dimethylphenol, 2,6-di-t-butylphenol, 2,4,6-tri-sec-butylphenol, 2,4,6-tri-t-butylphenol, 4-methyl-2,6-di-t-butylphenol, 4-methyl-3,5-di-t-butylphenol, hydroquinone, 2,5-di-t-butylhydroquinone, α-naphthol and β-naphthol; sulfonic acids such as benzenesulfonic acid and p-toluenesulfonic acid; mineral acids such as hydrochloric acid, sulfuric acid, phosphoric acid and boric acid, and Lewis acids such as aluminum chloride, zinc chloride, ferric chloride and boron trifluoride. Use of a fatty acid having 2 to 6 carbon atoms, a phenol or an aromatic carboxylic acid is preferred. The acid catalyst is used in an amount of 0.001 to 20% by weight, preferably 0.01 to 15% by weight, based on the starting 1-halogeno-3-alkene-2-ol of formula [II].

Use of a solvent is not particularly critical in the reaction (a), but if desired, solvents not participating in the reaction, such as n-octane, toluene, o-xylene m-xylene, p-xylene, di-n-butyl ether and tetralin may be used. When the ortho-carboxylic ester of above formula [III] is used in an amount excessive over the 1-halogeno-3-alkene-2-ol of formula [II], the ester [III] can act also as the solvent. It often happens that the ortho-carboxylic ester is decomposed to some extent during the reaction. Accordingly, even if it is not intended to make the ortho-carboxylic ester act as the solvent, it is preferred that the ortho-carboxylic ester be used in an amount of 1.3 to 3 moles per mole of the 1-halogeno-3-alkene-2-ol.

The reaction (a) is carried out under heating, generally at 100° to 200° C. and preferably at 120° to 160° C. When the temperature is lower than 100° C., the reaction rate is too low, and when the temperature is higher than 200° C., formation of by-products is increased. In order to prevent occurrence of side reactions, it is preferred to remove an alcohol formed as a by-product from the reaction system continuously and promptly.

(b) Reaction between 1-Halogeno-3-Alkene-2-Ol and Ketene Acetal:

As is apparent from the above reaction formula, it is possible to use a ketene acetal of above formula [IV] instead of the above-mentioned ortho-carboxylic ester of formula [III] in the reaction (i).

As is seen from the above reaction formula, the ketene acetal of formula [IV] can be prepared from a corresponding ortho-carboxylic ester (see R. H. Dewolfe, Carboxylic Ortho Acid Derivatives, page 276). Further, the ketene acetal of formula [IV] can be prepared by reaction between vinylidene chloride and sidium alcoholate (see S. R. Sandler et al, Organic Functional Group Preparation, Vol. III, page 48) or by reaction between bromoacetal and potassium t-butylate [see P. R. Johnson et al, J. Am. Chem. Soc., 62, 968 (1940)].

In the reaction between the ketene acetal of formula [IV] and the 1-halogeno-3-alkene-2-ol of formula [II], the presence of a catalyst is not particularly critical. Since the ketene acetal [IV] has generally a low boiling point and is readily evaporated, there is adopted a method in which the reaction temperature is gradually elevated as the addition reaction between the acetal [IV] and the 1-halogeno-3-alkene-2-ol [II] advances or a method in which the ketene acetal [IV] is gradually added to compensate for the acetal [IV] consumed as the reaction advances. In general, it is preferred that the ketene acetal be used in an amount 2 to 4 times the stoichiometrically necessary amount. Other conditions are substantially similar to those adopted when the ortho-carboxylic ester [III] is employed.

From the boiling point, NMR spectrum, IR spectrum and elementary analysis values of the intermediate formed according to the above reaction (a) or (b), it is believed that the intermediate is a γ-halogeno-δ-unsaturated-carboxylic ester having the above-mentioned general formula [V].

The γ-halogeno-δ-unsaturated carboxylic ester of formula [V] includes, for example, compounds illustrated below, each of which is considered to be a novel compound not introduced in the literature.

(1) Ethyl 3,3-dimethyl-4,6,6-trichloro-5-hexenoate
(2) Methyl 3,3-dimethyl-4,6,6-trichloro-5-hexenoate
(3) Ethyl 3,3-dimethyl-4,6,6-tribromo-5-hexenoate
(4) t-Butyl 3,3-dimethyl-4,6,6-tribromo-5-hexenoate
(5) Ethyl 2,2,3-trimethyl-4,6,6-trichloro-5-hexenoate
(6) n-Propyl 2,3,3-trimethyl-4,6,6-trichloro-5-hexenoate
(7) Ethyl 2,3,3-trimethyl-4,6,6-tribromo-5-hexenoate
(8) n-Octyl 2,3,3-trimethyl-4,6,6-tribromo-5-hexenoate
(9) Ethyl 3-methyl-4,6,6-trichloro-5-hexenoate
(10) Benzyl 3-methyl-4,6,6-trichloro-5-hexenoate
(11) Ethyl 3-methyl-4,6,6-tribromo-5-hexenoate
(12) Ethyl 3-methyl-3-ethyl-4,6,6-tribromo-5-hexenoate
(13) Cyclohexyl 3-methyl-3-ethyl-4,6,6-tribromo-5-hexenoate
(14) Ethyl 3-methyl-3-phenyl-4,6,6-trichloro-5-hexenoate
(15) Methyl 3-methyl-3-phenyl-4,6,6-trichloro-5-hexenoate
(16) Ethyl 3-methyl-3-benzyl-4,6,6-trichloro-5-hexenoate
(17) Ethyl 2-cyclohexyl-3,3-dimethyl-4,6,6-trichloro-5-hexenoate
(18) Ethyl 3,3-dimethyl-4,6-dichloro-5-hexenoate
(19) Methyl 3,3-dimethyl-4-chloro-5-hexenoate
(20) Benzyl 3,3-dimethyl-4,6,6-trichloro-5-hexenoate
(21) n-Octyl 3,3-dimethyl-4,6,6-tribromo-5-hexenoate
(22) m-Phenoxybenzyl 3,3-dimethyl-4,6,6-trichloro-5-hexenote
(23) m-Phenoxybenzyl 3,3-dimethyl-4,6,6-tribromo-5-hexenoate
(24) Pyrethronyl 3,3-dimethyl-4,6,6-trichloro-5-hexenoate
(25) Allethronyl 3,3-dimethyl-4,6,6-trichloro-5-hexenoate
(26) 5-Benzyl-3-furylmethyl 3,3-dimethyl-4,6,6-tribromo-5-hexenoate
(27) 5-Benzyl-3-furylmethyl 3,3-dimethyl-4,6,6-tribromo-5-hexenoate
(28) 3,4,5,6-Tetrahydrophthalimidomethyl 3,3-dimethyl 4,6,6-trichloro-5-hexenoate
(29) 5-Phenoxyfurfuryl 3,3-dimethyl-4,6,6-trichloro-5-hexenoate
(30) 5-Propargylfurfuryl 3,3-dimethyl-4,6,6-trichloro-5-hexenoate (ii) Ring Closure Reaction of Product Formed by Reaction (i)

When the reaction product formed by the above reaction (i) is treated with an organic or inorganic basic substance, it is readily converted to a corresponding substituted cyclopropane-carboxylic acid ester.

This reaction is represented by the following reaction formula:

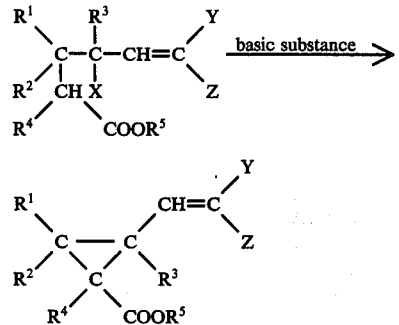

As the basic substance to be used for this reaction, there can be mentioned, for example, (1) alkali metal hydroxides such as sodium hydroxide and potassium hydroxide, (2) alkaline earth metal hydroxides such as calcium hydroxide and barium hydroxide, (3) alkali metal alcoholates such as sodium methylate, sodium ethylate, potassium methylate, potassium ethylate, sodium n-propylate, sodium n-butylate, sodium isoamylate, potassium t-butylate and potassium isoamylate, (4) nitro-containing organic bases such as 1,5-diazabicyclo[3,4,0]nonene-5 (abbreviated to "DBN"), 1,5-diazabicyclo[5,4,0]undecene-5 (abbreviated to "DBU"), 1,4-diazabicyclo[2,2,2]octane (abbreviated to "DABCO"), 2-dimethylamino-1-pyrroline and 5-methyl-1-azabicyclo[3,3,0]octane, (5) organolithium compounds such as n-butyllithium, sec-butyl lithium, diisopropylamino lithium and dicyclohexylamino lithium, (6) alkali metal hydrides such as sodium hydride and potassium hydride, (7) alkali metal amides such as sodium amide and potassium amide, and (8) alkali metals such as metallic sodium and metallic potassium.

The treatment of the product formed by the reaction (i) with a basic substance such as exemplified above is carried out at a temperature ranging from about −80° C. to about 100° C. It is preferred that when an alkali metal alcoholate, an alkali metal hydroxide or a nitrogen-containing organic base is used, the treatment be carried out at about 10° to about 100° C. and that when sodium hydride, sodium amide or the like is employed, the treatment can be carried out at −70° C. to +25° C.

Use of a solvent is not particularly critical in this reaction (ii), but it is possible to use, if desired, solvents not participating in the reaction, such as ethyl ether, tetrahydrofuran, benzene, toluene, methanol, n-propanol, isopropanol, n-butanol, t-butanol, n-hexane, n-octane, chlorobenzene, dichloro methane, ethyl acetate, carbon tetrachloride and acetonitrile.

When an alcohol is used as the solvent, as illustrated in Examples given hereinafter, it often happens that all or a part of the resulting substituted cyclopropane-carboxylic ester converts to a form of an ester of the substituted cyclopropane-carboxylic acid with the alcohol used as the solvent; namely, the resulting substituted cyclopropane-carboxylic acid ester is ester-exchanged with the alcohol used as the solvent.

When the product of the reaction (i) is treated with a basic substance such as mentioned above, a substituted cyclopropane-carboxylic ester represented by above general formula [I'] can be prepared. If desired, as illustrated in Examples given hereinafter, the resulting substituted cyclopropane-carboxylic ester [I'] is not isolated but converted to a corresponding substituted cyclopropane-carboxylic acid by adding water to the reaction mixture containing the ester [I'] to effect hydrolysis thereof. In this case, a water-soluble solvent such as methyl alcohol, ethyl alcohol or tetrahydrofuran is used as the solvent.

The basic substance is generally used in an amount of 0.3 to 7.0 moles per mole of the product of the reaction (i), namely the γ-halogeno-δ-unsaturated-carboxylic ester. In the case of the nitrogen-containing organic base, however, it is possible to use the organic base in great excess to make it act also as the solvent. In case the substituted cyclopropane-carboxylic ester formed by the reaction (ii) is hydrolyzed and a corresponding carboxylic acid is directly prepared, the intended object can be attained effectively by adding the basic substance in excess by an amount necessary for the hydrolysis and by neutralizing the aqueous layer after completion of the reaction (ii).

(iii) Conversion of Substituted Cyclopropane-Carboxylic Ester [I'] to Substituted Cyclopropane-Carboxylic Ester [I]

In case the substituted cyclopropane-carboxylic ester of formula [I'] prepared through the reaction steps (i) and (ii) has no insecticidal activity or only a very low insecticidal activity, it is desirable to convert the ester to an ester having a higher insecticidal activity.

This object can be attained by reacting the substituted cyclopropane-carboxylic ester of formula [I'] or a reactive derivative of said cyclopropane-carboxylic ester, such as a carboxylic acid, carboxylic anhydride, acid halide or salt of carboxylic acid with an alcohol represented by the following general formula $$R^{13}OH \qquad [VIII]$$

wherein $R^{13}$ is an alcohol residue included in $R^5$ as defined above, or a reactive derivative of said alcohol, such as a halide ($R^{13}X$, X = halogen atom), arylsulfonate or alkali metal alcoholate, in the presence of a suitable assistant to thereby form a cyclopropane-carboxylic acid ester represented by above-mentioned formula [I].

As the alcohol residue $R^{13}$ of the alcohol of above formula [VIII], there can be mentioned the same groups as exemplified above with respect to the alcohol residue $R^5$. Especially preferred examples of the alcohol [VIII] include those having an alcohol residue represented by the following general formula

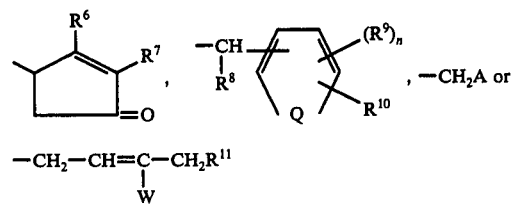

wherein $R^6$, $R^7$, $R^8$, $R^9$, $R^{10}$, $R^{11}$, Q, A, W and $n$ are as defined above with respect to the alcohol residue $R^5$ of the ortho-carboxylic ester.

As the alcohol of formula [VIII], there can be mentioned, for example, allethrolone, pyrethrolone, o-, m- or p-phenoxybenzyl alcohol, α-cyano-m-phenoxybenzyl alcohol, 3-benzylbenzyl alcohol, 5-phenoxyfurfuryl alcohol, 5-propargylfurfuryl alcohol, 5-benzyl-3-furylmethyl alcohol, α-cycano-5-benzyl-3-furylmethyl alcohol, 4-benzyl-2-butyn-1-ol, 3-phenyl-2-propyn-1-ol and 3,4,5,6-tetrahydrophthalimidomethyl alcohol.

Typical examples of this reaction (iii) are as follows:
(1) Ester exchange reaction.
(2) Reaction between an acid halide of the substituted cyclopropane-carboxylic acid and the alcohol.
(3) Reaction between the substituted cyclopropanecarboxylic acid and the alcohol.
(4) Reaction between a salt of the substituted cyclopropane-carboxylic acid and an arylsulfonate (for example, a tosylate) of the alcohol.

This step (iii) can be applied to the preparation of a substituted cyclopropane-carboxylic ester having an alcohol residue $R^{13}$ from a cyclopropane-carboxylic ester of formula [I'] in which the alcohol residue $R^5$ is a lower alkyl group such as a methyl, ethyl, propyl or butyl group.

Substituted cyclopropane-carboxylic esters represented by general formula [I] are compounds having a very excellent insecticidal activity and they can be effectively used as insecticides or other agricultural chemicals. Typical instances of the substituted cyclopropane-carboxylic ester represented by general formula [I] are as follows:
(1) 3-Phenoxybenzyl-2',2'-dimethyl-3'-(2",2"-dichlorovinyl)-cyclopropane-carboxylate
(2) 3,4,5,6-Tetrahydrophthalimidomethyl-2',2'-dimethyl-3'-(2",2"-dichlorovinyl)-cyclopropane-carboxylate
(3) 5-Benzyl-3-furylmethyl-2',2'-dimethyl-3'-(2",2"-dichlorovinyl)-cyclopropane-carboxylate (4) 3-Benzylbenzyl-2',2'-dimethyl-3'-(2",2"-dichlorovinyl)-cyclopropane-carboxylate
(5) 5-Phenoxyfurfuryl-2',2'-dimethyl-3'-(2",2"-dichlorovinyl)-cyclopropane-carboxylate
(6) 2-Allyl-3-methyl-2-cyclopenten-1-on-4-yl-2',2'-dimethyl-3'-(2",2"-dichlorovinyl)-cyclopropane-carboxylate
(7) 5-Propargylfurfuryl-2',2'-dimethyl-3'-(2",2"-dichlorovinyl)-cyclopropane-carboxylate
(8) α-Ethynyl-3-phenoxybenzyl-2',2'-dimethyl-3'-(2",2"-dichlorovinyl)-cyclopropane-carboxylate
(9) 3-Phenoxybenzyl-2',2'-dimethyl-3'-(2",2"-dibromovinyl)-cyclopropane-carboxylate
(10) 3,4,5,6-Tetrahydrophthalimidomethyl-2',2'-dimethyl-3'-(2",2"-dibromovinyl)-cyclopropane-carboxylate
(11) 5-Benzyl-3-furylmethyl-2',2'-dimethyl-3'-(2",2"-dibromovinyl)-cyclopropane-carboxylate
(12) 3-Phenoxybenzyl-2',2'-dimethyl-3'-(2"-monochlorovinyl)-cyclopropane-carboxylate
(13) 3-Phenoxybenzyl-1',2',2'-trimethyl-3'-(2",2"-dichlorovinyl)-cyclopropane-carboxylate
(14) 3-Phenoxybenzyl-2'-methyl-2'-phenyl-3'-(2",2"-dichlorovinyl)-cyclopropane-carboxylate
(15) 5-Benzyl-3-furylmethyl-2',2'-dimethyl-3'-vinylcyclopropane-carboxylate The ester exchange reaction between the cyclopropanecarboxylic ester of formula [I'] and the alcohol of formula [VIII] can be performed by using as a catalyst a basic substance such as one used at the step of the reaction (ii), e.g., an alkali metal alcoholate, and removing a lower alcohol formed by the reaction from the reaction system.

When an inert solvent such as benzene, toluene, n-octane, n-hexane or the like is used for this ester exchange reaction, the reaction can be advanced very smoothly.

The cyclopropane-carboxylic acid ester of general formula [I'] to be used for the reaction is one in which the group $R^5$ is a methyl, ethyl, n-propyl, isopropyl, n-butyl or t-butyl group.

When a cyclopropane-carboxylic acid is used as a reactive derivative of the cyclopropane-carboxylic ester of formula [I'] and it is reacted with an alcohol of formula [VIII], the reaction is carried out under anhydrous conditions.

In order to establish anhydrous conditions, the reaction is carried out under heating in the presence of an acid catalyst such as hydrochloric acid or sulfuric acid and a solvent capable of forming an azeotropic mixture with water, such as benzene or toluene to remove water formed by the reaction from the reaction system. It is also possible to use a dehydrating agent such as dicyclohexylcarbodiimide.

When a halide of a cyclopropane-carboxylic acid is used as a reactive derivative of the cyclopropane-carboxylic ester of formula [I'] and it is reacted with an alcohol of formula [VIII], if a tertiary amine such as pyridine or triethylamine is used as a dehydrohalogenating agent, the intended ester can be obtained under mild reaction conditions.

When a silver, lead or alkali metal salt of a cyclopropane-carboxylic acid is used as a reactive derivative of the cyclopropane-carboxylic ester of formula [I'] and it is reacted with an arylsulfonate of an alcohol of formula [VIII] as a reactive derivative of the alcohol [VIII], the reaction can be performed effectively in the presence of an inert solvent such as benzene, acetone, chloroform, ligroin or ether under heating at the boiling point of the solvent or a lower temperature.

This invention will now be described in detail by the following Examples that by no means limit the scope of this invention. In these Examples, all of "parts" are by weight.

EXAMPLE 1

0.1 Part of isobutyric acid was added to a mixture of 10.2 parts of 1,1,1-trichloro-4-methyl-3-penten-2-ol and 16.2 parts of ethyl ortho-acetate, and in an atmosphere of nitrogen, the mixture was agitated for 2 hours at 130° to 145° C. and for another 2 hours at 145° to 155° C. The alcohol formed as a by-product during the reaction was continuously distilled from the reaction system. After completion of the reaction, the liquid reaction mixture was directly subjected to distillation under reduced pressure to obtain 11.1 parts of a oily fraction having a boiling point of 83° to 84° C. under 0.28 mm Hg. The yield was 81% based on the starting 1,1,1-trichloro-4-methyl-3-penten-2-ol. Properties of the so obtained product were as follows:

IR Spectrum (liquid film method): 1610 cm$^{-1}$ (C=C), 1730 cm$^{-1}$ (CO)

NMR Spectrum (100 MHz) $\delta_{TMS4}^{CCl}$ 1.08 (s) 6H, 1.20 (t, J = 7Hz) 3H, 2.14 (d, J = 14Hz) 1H, 2.42 (d, J = 14Hz) 1H, 4.01 (q, J = 7Hz) 2H, 4.83 (d, J = 11Hz) 1H, 5.95 (d, J = 11Hz) 1H Elementary Analysis Values: Found: C = 43.77 %, H = 5.47% Calculated: C = 43.90%, H = 5.53%

From the foregoing properties, the so obtained compound was identified as ethyl 3,3-dimethyl-4,6,6-trichloro-5-hexenoate.

2.7 Parts of the so obtained compound was dissolved in 25 parts of dry benzene, and 1.9 parts of sodium t-butylate was added to the solution and the mixture was agitated at room temperature for 1 hour. The liquid reaction mixture was poured in ice water and extracted with ether. Ether and benzene were removed from the organic layer by distillation and the residue was subjected to distillation under reduced pressure to obtain 2.1 parts of intended ethyl 2,2-dimethyl-3-(2',2'-dichlorovinyl)-cyclopropane-carboxylate (the yield being 89%).

Properties of the so obtained compounds were as follows:

Boiling Point: 102° - 103° C. under 2.0 mm Hg
IR Spectrum (liquid film method): 1620 cm$^{-1}$ (C=C), 1730 cm$^{-1}$ (CO)
NMR Spectrum (100 MHz) $\delta_{TMS4}^{CCl}$: 1.15 (s), 1.20 (t, J = 7Hz), 1.22 (s) 9H; 1.47 (d, J = 5Hz) 1H; 2.10 (dd, J = 5.8Hz) 1H, 4.03 (q, J = 7Hz) 2H; 5.52 (d, J = 8Hz) 1H Elementary Analysis Values: Found: C = 50.51%, H = 6.24% Calculated: C = 50.65%, H = 5.95%

Mass Spectrum, m/e (M$^+$.): 236, 238, 240

EXAMPLE 2

The procedure of Example 1 was repeated by using 0.4 part of phenol instead of isobutyric acid, to obtain 9.7 parts of an oily fraction having a boiling point of 83° - 84° C. under 0.28 mm Hg.

0.5 Part of the so obtained oily substance (considered to be ethyl 3,3-dimethyl-4,6,6-trichloro-5-hexenoate) was dissolved in 10 parts of dry tetrahydrofuran, and 0.4 part of powdery potassium hydroxide was added to the solution and the mixture was agitated at 45° to 50° C. for 1.5 hours.

The liquid reaction mixture was directly filtered by using Celite to remove solids. Tetrahydrofuran was removed from the filtrate by distillation. When the resulting oily substance was analyzed by gas chromatography, it was found that intended ethyl 2,2-dimethyl-3-(2',2'-dichlorovinyl)-cyclopropane-carboxylate was formed in a yield of about 20%.

EXAMPLE 3

20 Parts of o-xylene as a solvent was added to a mixture of 2.0 parts of 1,1,1-trichloro-4-methyl-3-penten-2-ol and 4.6 parts of ketene diethyl acetal ( having a boiling point of 80° - 85° C. under 200 mm Hg ), and the temperature of the mixture was gradually elevated to 145° C. over a period of 1.5 hours. At this point, 0.01 part of isobutyric acid was added to the mixture, and the mixture was agitated at the above temperature for 5 hours. The liquid reaction mixture was subjected to distillation under reduced pressure to obtain 2.2 parts of an oily substance ( having a boiling point of 83° - 84° C. under 0.28 mm Hg ) similar to that obtained in Example 1.

Then, 0.5 part of the so obtained intermediate (A) ( ethyl 3,3-dimethyl-4,6,6-trichloro-5-hexenoate ) was added to 5 parts of 1,5-diazabicyclo[5.4.0]undecene-5 ( DBU ), and the mixture was agitated at 45° to 50° C. for 1 hour. The liquid reaction mixture was sufficiently shaken with about 50 parts of water, and the lower organic layer was analyzed by gas chromatography. It was found that intended ethyl 2,2-dimethyl-3-(2',2'-dichlorovinyl)-cyclopropane-carboxylate was formed in a yield of about 15%.

EXAMPLE 4

1.4 Parts of metallic sodium was dissolved in 50 parts of anhydrous methanol, and 5.5 parts of ethyl 3,3-dimethyl-4,6,6-trichloro-5-hexenoate prepared in the same manner as in Example 1 was added to the solution. The mixture was agitated for 2 hours under reflux of methanol. The liquid reaction mixture was naturally cooled, and 20 parts of water was added thereto and the mixture was agitated at 40° to 50° C. for 2 hours. Then, methanol was distilled under reduced pressure, and the residue was neutralized with hydrochloric acid and extracted with diethyl ether. The ether extract was dried and the ether was distilled to obtain 3.7 parts of the crystal of 2,2-dimethyl-3-(2',2'-dichlorovinyl)-cyclopropane-carboxylic acid. The yield was 88% based on ethyl 3,3-dimethyl-4,6,6-trichlorohexenoate.

The cis : trans ratio of the product determined by NMR spectrum was 28 : 72. When this crystal was fractionally recrystallized from n-hexane, it could be divided into the cis-isomer having a melting point of 88° - 89° C. and the trans-isomer having a melting point of 94°-96° C. The results of the NMR spectrum ( 60 MHz ) analysis of the pure trans-isomer were as follows:

$\delta_{TMS}$: 1.18 (s) 3H, 1.30 (s) 3H, 1.53 ( d, J = 5.5Hz) 1H, 2.20 ( dd, J = 8Hz & 5.5Hz ) 1H, 5.58 ( d, J = 8Hz) 1H

EXAMPLE 5

1.1 Parts of potassium hydroxide was dissolved in 30 parts of anhydrous methanol, and 2.7 parts of ethyl 3,3-dimethyl-4,6,6-trichloro-5-hexenoate prepared in the same manner as described in Example 2 was added to the solution. The mixture was agitated for 2 hours under reflux of methanol. The liquid reaction mixture was diluted with about 100 parts of diethyl ether and washed with about 25 parts of water. The aqueous layer was extracted three times with diethyl ether. The recovered diethyl ether extract was subjected to distillation to remove low-boiling-point substances therefrom and recover 1.0 part ( the yield being 45% ) of methyl 2,2-dimethyl-3-(2',2'-dichlorovinyl)-cyclopropane-carboxylate having properties described below.

The cis : trans ratio of the product determined by gas chromatography was 35 : 65.

Boiling Point: 67° - 68° C. under 0.2 mm Hg

NMR Spectrum ( 60 MHz ) $\delta_{TMS}$: 1.12 - 1.25 (m) 6H; 1.42 - 2.25 (m) 2H; 3.60 (s) 3H; 5.57 ( d, J = 8.5 Hz ), 6.23 ( d, J = 8.5 Hz ) 1H When the above aqueous layer was neutralized with hydrochloric acid and extracted with diethyl ether, there was obtained 0.8 part of 2,2-dimethyl-3-(2',2'-dichlorovinyl)-cyclopropane-carboxylic acid. The yield was 38%. When the product was analyzed in the same manner as in Example 4, it was found that the cis : trans ratio was 21 : 79.

EXAMPLE 6

0.4 Part of metallic sodium was dissolved in 30 parts of anhydrous methanol, and 2.7 parts of ethyl 3,3-dimethyl-4,6,6-trichloro-5-hexenoate prepared in the same manner as in Example 3 was added to the solution. The mixture was agitated for 2 hours under reflux of methanol. The liquid reaction mixture was cooled with ice water and neutralized with hydrogen chloride-saturated methanol. The precipitated solids were removed by filtration, and the filtrate was concentrated until the volume was reduced to 1/10. The concentrate was diluted with diethyl ether, washed with water and dried. Then, the solvent was removed by distillation, and the residue was subjected to distillation under reduced pressure to obtain 2.0 parts of methyl 2,2-dimethyl-3-(2',2'-dichlorovinyl)-cyclopropane-carboxylate having a boiling point of 68° - 70° C. under 0.2 mm Hg. The yield was 90%. the cis : trans ratio of the product determined by gas chromatography was 22 : 78.

EXAMPLE 7

0.4 Part of metallic sodium was dissolved in 20 parts of anhydrous ethanol, and 2.7 parts of ethyl 3,3-dimethyl-4,6,6-trichloro-5-hexenoate was added to the solution. The mixture was agitated for 2 hours under reflux of ethanol. The liquid reaction mixture was diluted with about 50 parts of diethyl ether and neutralized with dried hydrogen chloride gas. The precipitated crystal of sodium chloride was removed by filtration and low-boiling-point substances were removed from the filtrate by distillation. The residue was then subjected to distillation under reduced pressure to obtain 2.1 parts of ethyl 2,2-dimethyl-3-(2',2'-dichlorovinyl)-cyclopropane-carboxylate having a boiling point of 72° - 73° C. under 0.3 mm Hg. The yield was 87%. The properties of the product were in agreement with those of ethyl 2,2-dimethyl-3-(2',2'-dichlorovinyl)-cyclopropane-carboxylate described in Example 1.

EXAMPLE 8

1.80 Parts of ethyl 2,2-dimethyl-3-(2',2'-dichlorovinyl)-cyclopropane-carboxylate prepared in the same manner as in Example 1 was agitated at 40° to 50° C. for 3 hours in the presence of 8.65 parts of a 10% solution of potassium hydroxide and methanol to effect hydrolysis of the ester and obtain 1.43 parts of 2,2-dimethyl-3-(2',2'-dichlorovinyl)-cyclopropane-carboxylic acid, the data of the melting point and NMR spectrum of which were in agreement with the data described in Example 4.

1.43 Parts of the so obtained carboxylic acid was agitated at 80° C. for 30 minutes together with 0.98 part of thionyl chloride in benzene as a solvent to obtain 2,2-dimethyl-3-(2',2'-dichlorovinyl)-cyclopropane-carboxylic acid chloride. The so obtained compound was agitated at room temperature for 1 hour together with 1.37 parts of 3-phenoxybenzyl alcohol in the presence of pyridine in benzene as a solvent, to obtain 2.63 parts of 3-phenoxybenzyl-2',2'-dimethyl-3'-(2'',2''-dichlorovinyl)-cyclopropane-carboxylate ( $n_D^{20}$ = 1.5615 ). The results of the NMR spectrum ( 60 MHz ) analysis of the so obtained compound were as follows:

$\delta_{TMS}^{CCl_4}$: 1.10 (s) 3H; 1.19, 1.21 ( each s ) 3H; 1.52 ( d, J = 5.5Hz ) 1H; 2.16 ( dd, J = 8Hz & 5.5 Hz ) 1H; 5.01 (s) 2H; 5.54 ( d, J = 8Hz ) 1H; 6.8 - 7.5 (m) 9H

EXAMPLE 9

0.03 Part of isobutyric acid was added to a mixture of 4.1 parts of 1,1,1-trichloro-4-methyl-3-penten-2-ol and 7.0 parts of ethyl ortho-propionate, and the mixture was agitated at 130° to 145° C. for 4 hours in an atmosphere of nitrogen. Ethyl alcohol formed as a by-product was continuously distilled from the reaction mixture during the reaction. After completion of the reaction, the liquid reaction mixture was directly subjected to distillation under reduced pressure to obtain 4.9 parts of a fraction of an oily substance having a boiling point of 92° - 99° C. under 0.25 mm Hg. By gas chromatography of the product, it was found that the product was composed of two elements.

Accordingly, the product was subjected to column chromatography on silica gel using benzene as a developing liquid and 1.6 parts of a compound having the following properties was obtained.

Boiling Point: 104°- 106° C. under 0.4 mm Hg
IR Spectrum ( liquid film method ): 1610 cm$^{-1}$( C=C ), 1730 cm$^{-1}$ ( CO )
NMR Spectrum ( 100 MHz ) $\delta_{TMS}^{CCl_4}$: 1.20 ( t, J = 7Hz ), 0.9 - 1.3, 12H; 2.4 - 2.7 (m) 1H; 4.01 ( q, J = 7Hz ), 4.03 ( q, J = 7Hz ) 2H; 4.63 ( d, J = 11Hz ), 4.78 ( d, J = 11Hz ) 1H; 5.96 ( d, J 32 11Hz ), 5.97 ( d, J =11Hz ) 1H Elementary Analysis Values: Found: C = 46.20%, H = 6.02% Calculated: C = 45.94%, H = 5.96%

In view of the foregoing properties, it was construed that the above product was ethyl 2,3,3-trimethyl-4,6,6-trichloro-5-hexenoate.

1.0 Part of this compound was dissolved in 5 parts of dry benzene, and 0.67 part of sodium t-butylate was added to the solution and the mixture was agitated under reflux of benzene for 30 minutes. The liquid reaction mixture was poured in ice water and extracted with diethyl ether and the ether and benzene were distilled from the organic layer to obtain 0.72 part of ethyl 1,2,2-trimethyl-3-(2',2'-dichlorovinyl)-cyclopropane-carboxylate as an oily product. The yield was 82%. The results of the NMR spectrum ( 60 MHz ) analysis were as follows:

$\delta_{TMS}^{CCl_4}$: 1.04 (s), 1.13 (s), 1.18 (s), 1.23 ( t, J = 7Hz ) 12H; 2.25 ( d, J = 8Hz ) 1H; 4.08 ( q, J = 7Hz ) 2H; 5.57 ( d, J = 8Hz ) 1H 0.72 Part of the above ester was agitated at 40° - 50° C. for 3 hours in the presence of 3.26 parts of a 10% aqueous solution of sodium hydroxide and methyl alcohol to effect hydrolysis of the ester and obtain 0.60 part of 1,2,2-trimethyl-3-(2',2'-dichlorovinyl)-cyclopropanecarboxylic acid.

Properties of the so obtained compound were as follows:

Melting Point: 137° - 138° C.
NMR Spectrum ( 60 MHz ) $\delta_{TMS}^{CCl_4}$: 1.08 (s), 1.22 (s) 1.25 (s) 9H; 2.33 ( d, J = 8Hz ) 1H; 5.56 ( d, J = 8Hz) 1H
IR Spectrum ( KBr disk): 1685 cm$^{-1}$( CO ).

0.60 Part of the above carboxylic acid was agitated with 0.38 part of thionyl chloride at 80° C. for 30 minutes in benzene as a solvent to obtain 1,2,2-trimethyl-3-(2',2',-dichlorovinyl)-cyclopropane-carboxylic acid chloride. The acid chloride was agitated with 0.53 part of 3-phenoxybenzyl alcohol in the presence of pyridine at room temperature in benzene as a solvent to obtain 1.02 parts of 3-phenoxybenzyl-1',2',2'-trimethyl-3'-(2'',2''-dichlorovinyl)-cyclopropane-carboxylate. The results of the NMR spectrum ( 60 MHz ) analysis of the so obtained product were as follows:

$\delta_{TMS}^{CCl_4}$: 0.94 (s) 3H, 1.05 (s) 3H; 1.12,1.13 ( each s ) 3H; 2.29 ( d, J =8Hz ) 1H; 4.99 (s) 2H; 5.54 ( d, J = 8Hz ) 1H; 6.7 - 7.4 (m) 9H

EXAMPLE 10

By the ester-exchange of the intermediate prepared in Example 1 ( ethyl 3,3-dimethyl-4,6,6-trichloro-5-hexenoate ), there were obtained 5-benzyl-3-furylmethyl ester [IX], m-phenoxybenzyl ester [X] and allethronyl ester [XI] of 3,3-dimethyl-4,6,6-trichloro-5-hexenoic acid. The so obtained ester in an amount indicated in Table 1 given below was dissolved in 30 parts of dry benzene, and a prescribed amount of sodium t-butylate or potassium t-butylate was added to the solution and the mixture was agitated for 20 minutes under reflux of benzene. The liquid reaction mixture was poured in ice water and promptly extracted with diethyl ether. The ether and benzene were distilled from the organic layer and the residue was subjected to column chromatography to obtain the corresponding ester of 2,2-dimethyl-3-(2',2'-dichlorovinyl)-cyclopropane-carboxylic acid, namely 5-benzyl-3-furylmethyl ester [IX'], m-phenoxybenzyl ester [X'] or alletronyl ester [XI'].

Table 1

| Starting Compound | Basic Substance | Product |
|---|---|---|
| [IX], 3.8 parts | t-BuONa, 1.9 parts | [IX'], m. p. = 55° C. |
| [X], 3.9 parts | t-BuOK, 2.2 parts | [X'], $n_C^{20}$ = 1.5615 |
| [XI], 3.4 parts | t-BuOK, 2.2 parts | [XI'], $n_D^{20}$ = 1.5142 |

EXAMPLE 11

0.3 Part of isobutyric acid was added to a mixture of 33.7 parts of 1,1,1-tribromo-4-methyl-3-penten-2-ol and 48.7 parts of ethyl ortho-acetate, and in an atmosphere of nitrogen the mixture was agitated for 2 hours at 130° to 145° C. and for another 2 hours at 145° to 155° C. Ethyl alcohol formed as a by-product by the reaction was continuously distilled from the reaction system during the reaction. The liquid reaction mixture was directly subjected to distillation under reduced pressure to obtain a fraction of an oily substance having a boiling point of 125° - 127° C. under 0.25 mm Hg. Thus, there was recovered 28.3 parts of ethyl 3,3-dimethyl-4,6,6-tribromo-5-hexenoate. The yield was 70% based on 1,1,1-tribromo-4-methyl-3-penten-2-ol. Physical properties of the product were as follows:

IR Spectrum ( liquid film method ) : 1600 cm$^{-1}$ ( C=C ), 1730 cm$^{-1}$ ( CO )

NMR Spectrum ( 60 MHz ) $\delta_{TMS4}{}^{CCl}$: 1.12 (s) 6H, 1.22 ( t, J = 7Hz ) 3H, 2.17 ( d, J = 15Hz ) 1H, 2.49 ( d, J = 15Hz ) 1H, 4.08 ( q, J = 15Hz ) 1H, 2.49 ( d, J = 15Hz ) 1H, 4.08 ( q, J = 7Hz ) 2H, 4.93 ( d, J = 11Hz ) 1H, 6.66 ( d, J = 11Hz ) 1H 4.1 Parts of the so obtained ethyl 3,3-dimethyl-4,6,6tribromo-5-hexenoate was dissolved in 35 parts of dry benzene, and 1.9 parts of sodium t-butylate was added to the solution and the mixture was agitated for 1 hour under reflux of benzene. The liquid reaction mixture was poured into ice water and extracted with diethyl ether, and ether and benzene were distilled from the organic layer. The residue was subjected to distillation under reduced pressure to obtain 3.2 parts of ethyl 2,2-dimethyl-3-(2',2'-dibromovinyl)-cyclopropane-carboxylate having a boiling point of 92° - 94° C. under 0.5 mm Hg. The yield was 98%.

Physical properties of the so obtained compound were as follows:

IR Spectrum ( liquid film method ): 1600 cm$^{-1}$( C=C ), 1730 cm$^{-1}$ ( CO )

NMR Spectrum ( 100 MHz ) $\delta_{TMS4}{}^{CCl}$: 1.19 (s), 1.23 ( t, J =7Hz ), 1.26 (s) 9H; 1.53 ( d, J = 5Hz ) 1H; 2.08 ( dd, J = 5Hz & 8Hz ) 1H, 4.03 (q, J = 7Hz) 2H; 6.04 ( d, J = 8Hz) 1H

EXAMPLE 12

2.02 Parts of ethyl 2,2-dimethyl-3-(2',2'-dibromovinyl)-cyclopropane-carboxylate obtained in Example 11 was agitated with 7.06 parts of a 10% aqueous solution of potassium hydroxide in the presence of ethyl alcohol at 40° to 50° C. for 2 hours to effect hydrolysis of the ester and obtain 1.08 parts of 2,2-dimethyl-3-(2',2'-dibromovinyl)-cyclopropane-carboxylic acid having a melting point of 116° - 117° C.

1.08 Parts of the so obtained cyclopropane-carboxylic acid was agitated with 0.68 part of thionyl chloride at room temperature for 30 minutes in benzene as a solvent to obtain 2,2-dimethyl-3-(2',2'-dibromovinyl)-cyclopropane-carboxylic acid chloride. The acid chloride was agitated with 0.68 part of 5-benzyl-3-furylmethyl alcohol in the presence of pyridine in benzene as a solvent at room temperature for 1 hour to obtain 1.69 parts of intended 5-benzyl-3-furylmethyl-2',2'-dimethyl-3'-(2'',2''-dibromovinyl)-cyclopropane-carboxylate.

Physical properties of the so obtained ester were as follows:

Melting Point: 62° - 63° C.
IR Spectrum (KBr disk): 1730 cm$^{-1}$ (CO)

EXAMPLE 13

2.5 Parts of 2,2-dimethyl-3-(2',2'-dibromovinyl)-cyclopropane-carboxylic acid prepared in the same manner as described in Example 12 was dissolved in dry benzene, and a solution of 4.0 parts of 5-benzyl-3-furylmethyl alcohol in dry benzene was added to the above benzene solution in the dark. Then, 3.0 parts of dicyclohexylcarbodiimide was added to the mixture and the mixture was allowed to stand still for 2 days. The resulting precipitate was removed by filtration and benzene was distilled from the filtrate. When the so obtained oily product was analyzed by column chromatography, it was found that there was formed 5-benzyl-3-furylmethyl-2',2'-dimethyl-3'-(2'',2''-dibromovinyl)-cyclopropane-carboxylate having a melting point of 62° to 63° C. The structure of the product was confirmed by the IR spectrum and NMR spectrum analysis.

EXAMPLE 14

The procedure of Example 1 was repeated by using 1,1-dichloro-4-methyl-3-penten-2-ol instead of 1,1,1-trichloro-4-methyl-3-penten-2-ol to prepare ethyl 3,3-dimethyl-4,6-dichloro-5-hexenoate. Then, the so obtained ester was treated with sodium t-butylate under reflux of benzene to prepare ethyl 2,2-dimethyl-3-(2'-chlorovinyl)-cyclopropane-carboxylate. The structure of the ester was confirmed by the IR spectrum and NMR spectrum analysis.

EXAMPLE 15

In Example 11, 1,1,1-tribromo-4-methyl-3-hepten-2-ol was used instead of 1,1,1-tribromo-4-methyl-3-penten-2-ol, and ethyl 3-methyl-3-propyl-4,6,6-tribromo-5-hexenoate was prepared in the same manner as described in Example 11. The ester was treated with sodium t-butylate under reflux of benzene to prepare ethyl 2-methyl-2-propyl-3-(2',2'-dibromovinyl)-cyclopropane-carboxylate. The structure of the ester was confirmed by the NMR spectrum analysis.

EXAMPLE 16

In benzene as a solvent, 1.56 parts of 2,2-dimethyl-3-(2',2'-dichlorovinyl)-cyclopropane-carboxylic acid chloride prepared in the same manner as in Example 8 and 1.04 parts of allethrolone were agitated in the presence of pyridine at room temperature for 1 hour to obtain 2.28 parts of allethronyl-2,2-dimethyl-3-(2',2'-dichlorovinyl)-cyclopropane-carboxylate. The results of the NMR spectrum analysis of the so obtained ester were as follows:

NMR Spectrum (60 MHz) $\delta_{TMS4}{}^{CCl}$: 1.18 (s) 3H; 1.25, 1.26 (each s) 3H; 1.53 (d, J = 5Hz) 1H; 1.94 (bs) 3H; 2.0 - 3.0 (m) 5H; 4.7 - 5.8 (m) 5H

EXAMPLE 17

To 61.2 parts of 1,1,1-trichloro-4-methyl-4-pentene-2-ol, 0.06 part of p-toluenesulfonic acid was added and the mixture was heated at 115° C. for 1.5 hours with stirring. Then, 97.3 parts of ethyl ortho acetate was added in the reaction mixture and said mixture was heated at 130° - 145° C. for 2 hours and for another 4 hours at 145° - 155° C. with stirring. The alcohol formed as a by-product during the reaction was continuously distilled from the reaction system. The reaction mixture was subjected to the same treatment disclosed in Example 1 to obtain 42.6 parts of ethyl 3,3-dimethyl-4,6,6-trichloro-5-hexenoate having the boiling point of 83° - 84° C. under 0.28 mm Hg. The yield was 52 weight % based on the starting 1,1,1-trichloro-4-methyl-4-penten-2-ol.

Ethyl 2,2-dimethyl-3-(2',2'-dichlorovinyl)cyclopropane carboxylate was obtained from ethyl 3,3-dimethyl-4,6,6-trichloro-5-hexenoate by the same manner discribed in Example 1.

EXAMPLE 18

To the mixture of 61.2 parts of 1,1,1-trichloro-4-methyl-4-pentene-2-ol and 120 parts of toluene, 1.2 parts of p-toluenesulfonic acid were added and the whole mixture was heated under reflux for 1.5 hours with stirring. Then, 97.3 parts of ethyl orthoacetate were added in the reaction mixture and said mixture was heated at 11.0° - 120° C. for 2 hours and for another 4 hours at 120° - 155° C. The alcohol formed as a by-product during the reaction was continuously distilled from the reaction system. The reaction mixture was subjected to the same treatment disclosed in Example 1 to obtain 52.5 parts of ethyl 3,3-dimethyl-4,6,6-trichloro-5-hexenoate. The yield was 64% based on the weight of the used 1,1,1-trichloro-4-methyl-4-pentene-2-ol.

Ethyl 2,2-dimethyl-3-(2',2'-dichlorovinyl)cyclopropane carboxylate was obtained from ethyl 3,3-dimethyl-4,6,6-trichloro-5-hexenoate, thus obtained, by the same manner described in Example 1.

EXAMPLE 19

10.2 parts of 1,1,1-trichloro-4-methyl-3-pentene-2-ol were added to 16.2 parts of ethyl orthoacetate, and in atmosphere of nitrogen, the mixture was agitated for 2 hours at 130° to 145° C. and for another 8 hours at 145° to 155° C. The alcohol formed as a by-product during the reaction was continuously distilled from the reaction system. After completion of the reaction, the liquid reaction mixture was directly subjected to distillation under reduced pressure to obtain 11.4 parts of ethyl 3,3-dimethyl-4,6,6-trichloro-5-hexenoate having a boiling point of 83° to 84° C. under 0.28 mm Hg. The yield was 81% based on the starting 1,1,1-trichloro-4-methyl-3-pentene-2-ol.

Ethyl 2,2-dimethyl-3-(2',2'-dichlorovinyl)cyclopropane carboxylate was obtained from ethyl 3,3-dimethyl-4,6,6-trichloro-5-hexenoate, thus obtained, by the same manner disclosed in Example 1.

EXAMPLE 20

33.7 Parts of 1,1,1-tribromo-4-methyl-3-pentene-2-ol were added to 48.7 parts of ethyl orthoacetate, and in atmosphere of nitrogen, the mixture was agitated for 2 hours at 130° - 145° C. and for another 8 hours at 145° - 155° C. The alcohol formed as a by-product during the reaction was continuously distilled from the reaction system.

After completion of the reaction, the liquid reaction mixture was directly subjected to distillation under reduced pressure to obtain 29.1 parts of ethyl 3,3-dimethyl-4,6,6-tribromo-5-hexenoate as an oily product. The yield was 72% based on the starting 1,1,1-tribromo-4-methyl-3-pentene-2-ol.

Ethyl 2,2-dimethyl-3-(2',2'-dibromovinyl)cyclopropane carboxylate was obtained from ethyl 3,3-dimethyl-4,6,6-tribromo-5-hexenoate, thus obtained, by the same manner described in Example 11.

The preparation of allyl type alcohols of above general formula [II] to be used in practicing the process of this invention will now be illustrated by the following Referential Examples, in which all of "parts" are by weight.

REFERENTIAL EXAMPLE 1

33 Parts of 1,1,1-trichloro-4-methyl-4-penten-2-ol (having a purity higher than 98%) was agitated at 140° to 150° C. in an atmosphere of nitrogen for a prescribed period of time, and when the obtained product was analyzed by gas chromatography, it was found that intended 1,1,1-trichloro-4-methyl-3-penten-2-ol was formed at conversion and selectivity shown in Table 2 given below.

Table 2

| Reaction Time (hours) | Conversion (%) | Selectivity (%) |
|---|---|---|
| 19 | 76 | 95 |

Table 2-continued

| Reaction Time (hours) | Conversion (%) | Selectivity (%) |
|---|---|---|
| 24 | 82 | 94 |
| 30 | 86 | 94 |
| 34 | 86 | 94 |

The product obtained by conducting the treatment for 34 hours was subjected to distillation under reduced pressure to obtain a fraction of a solid having a boiling point of 105° - 120° C. under 18 mm Hg, and the so recovered solid was recrystallized from n-hexane to thereby isolate pure 1,1,1-trichloro-4-methyl-3-penten-2-ol, the properties of which were as follows:

Melting Point: 83° C.

IR Spectrum (KBr disk): 1670 cm$^{-1}$ (C=O), 3270 cm$^{-1}$ (OH)

NMR Spectrum (60 MHz) $\delta_{TMS}^{CCl_4}$: 1.78 (s) 6H, 2.63 (bs) 1H, 4.60 (d, J = 9Hz) 1H, 5.29 (bd, J = 9Hz) 1H, Elementary Analysis Values: Found: C = 35.56%, H = 4.47% Calculated: C = 35.41%, H = 4.46%

REFERENTIAL EXAMPLE 2

1 Part of palladium black was added to 100 parts of 1,1,1-trichloro-4-methyl-4-penten-2-ol (having a purity higher than 98%), and the mixture was agitated for 18 hours at 140° to 150° C. in an atmosphere of nitrogen. As a result of the gas chromatography analysis of the product it was found that isomerization to intended 1,1,1-trichloro-4-methyl-3-penten-2-ol was accomplished at a conversion of 83% and a selectivity of 94%. The resulting reaction mixture was diluted with ether, washed with water and filtered to remove the catalyst. The ether layer was dried with magnesium sulfate and subjected to distillation under reduced pressure to recover 90 parts of a fraction of a solid having a boiling point of 110° - 115° C. under 20 mm Hg. The solid was recrystallized from n-nexane to isolate pure 1,1,1-trichloro-4-methyl-3-peten-2-ol.

REFERENTIAL EXAMPLES 3 TO 18 AND COMPARATIVE EXAMPLE 1

To 2 parts of 1,1,1-trichloro-4-methyl-4-peten-2-ol was added at least one substance selected from the group consisting of transition metals of the groups 6B, 7B and 8 of the Periodic Table and compounds of these transition metals in an amount of 5% by weight based on starting 1,1,1-trichloro-4-methyl-4-penten-2-ol, and the mixture was agitated at 140° to 150° C. for 4 hours. The reaction product was analyzed by gas chromatography to examine the conversion and selectivity of intended 1,1,1-trichloro-4-methyl-3-penten-2-ol. Results are shown in Table 3. For comparison, the isomerization of 1,1,1-trichloro-4-methyl-4-penten-2-ol was conducted under the same conditions but no catalyst was employed (Comparative Example 1).

Table 3

| | Catalyst | Conversion (%) | Selectivity (%) of 1,1,1-Trichloro-4-Methyl-3-Penten-2-Ol |
|---|---|---|---|
| Comparative Example 1 | not added | about 30 | about 90 |
| Referential Example 3 | chromium (III) acetylacetonate | 75 | 85 |

Table 3-continued

| Catalyst | Conversion (%) | Selectivity (%) of 1,1,1-Trichloro-4-Methyl-3-Penten-2-ol |
|---|---|---|
| Referential Example 4 | molybdenum disulfide | 75 | 80 |
| Referential Example 5 | tungsten trioxide | 45 | 95 |
| Referential Example 6 | manganese (III) acetylacetonate | 60 | 90 |
| Referential Example 7 | ruthenium trichloride | 75 | 60 |
| Referential Example 8 | cobalt (II) acetylacetonate | 80 | 85 |
| Referential Example 9 | hexamminecobalt chloride | 80 | 95 |
| Referential Example 10 | rhodium (III) acetylacetonate | 80 | 90 |
| Referential Example 11 | rhodium trichloride | 45 | 90 |
| Referential Example 12 | iridium trichloride | 70 | 95 |
| Referential Example 13 | Raney nickel | 65 | 85 |
| Referential Example 14 | nickel (II) acetylacetonate | 80 | 80 |
| Referential Example 15 | palladium chloride | 80 | 85 |
| Referential Example 16 | palladium black | 80 | 95 |
| Referential Example 17 | palladium oxide | 80 | 95 |
| Referential Example 18 | 1 : 1 mixture of cobalt (II) acetylacetonate and nickel (II) acetylacetonate | 80 | 80 |

REFERENTIAL EXAMPLE 19

A mixture of 281 parts of tribromoacetaldehyde, 168 parts of isobutene and 150 parts of petroleum ether was cooled to − 20° to − 5° C., and 13 parts of anhydrous aluminum chloride was added to the mixture dividedly in several times. The mixture was agitated at the above temperature for 5 hours. As the reaction advanced, crystals were precipitated from the reaction mixture. At the point of termination of the reaction, diethyl ether was added to the reaction mixture to form a homogeneous solution. The solution was then agitated at room temperature for 30 minutes, and 200 parts of water was added to the reaction mixture. The organic layer was recovered, low-boiling-point substances were removed by distillation, and the residue was subjected to distillation under reduced pressure to obtain 287 parts of 1,1,1-tribromo-4-methyl-4-penten-2-ol. The yield was 85%.

IR Spectrum (KBr disk): 1645 cm$^{-1}$ (C=C), 3500 cm$^{-1}$ (OH)

NMR Spectrum (60 MHz) $\delta_{TMS^4}^{CCl}$: 1.82 (s) 3H; 2.03 − 3.05 (m) 2H; 3.87 − 4.10 (m) 1H; 4.88 (s) 2H 50 Parts of the so obtained 1,1,1-tribromo-4-methyl-4-penten-2-ol (having a purity higher than 98%) was agitated at 130° to 135° C. for 5 hours in an atmosphere of nitrogen. When the product was analyzed by gas chromatography, it was found that intended 1,1,1-tribromo-4-methyl-3-penten-2-ol was formed at a conversion of 88% and a selectivity of 97%. The reaction product was dissolved in diethyl ether and the solution was treated with active carbon to effect decolorization. Diethyl ether was then removed by distillation, and the residual solid was recrystallized from petroleum ether to obtain 38 parts of 1,1,1-tribromo-4-methyl-3-penten-2-ol having a melting point of 81.5° to 82° C.

Boiling Point: 120° − 122° C. under 1 mm Hg

IR Spectrum (KBr disk): 1670 cm$^{-1}$ (C=C), 3310 cm$^{-1}$ (OH)

NMR Spectrum (60 MHz) $\delta_{TMS^4}^{CCl}$: 1.80 (s) 6H, 2.71 (d, J = 6Hz) 1H, 4.38 − 4.68 (m) 1H, 5.30 (bd, J = 8Hz) 1H

REFERENTIAL EXAMPLE 20

To 100 parts of n-nexane, 50 parts of 1,1,1-trichloro-4-methyl-4-pentene-2-ol and 1.0 part of p-toluenesulfonic acid were added and the whole was heated under reflux for 15 hours. The contents of the reaction vessel were analyzed by gas chromatography to reveal that aimed 1,1,1-trichloro-4-methyl-3-pentene-2-ol was formed. Conversion was 85% and selectivity was 96%. Upon allowing the contents to cool, crystals were formed. The crystals were 1,1,1-trichloro-4-methyl-3-pentene-2-ol of the same properties as in Referential Example 1. After filtration, yield of the product was 31 parts.

The mother liquor obtained by the filtration was a mixture of 1,1,1-trichloro-4-methyl-4-pentene-2-ol and 1,1,1-trichloro-4-methyl-4-methyl-3-pentene-2-ol (about 1:1), which was then subjected directly to heating under reflux to carry out the isomerization further to attain ratio of the isomers of about 2:8.

REFERENTIAL EXAMPLE 21

To 25 parts of toluene, 5 parts of 1,1,1-tribromo-4-methyl-4-pentene-2-ol and 0.1 part of p-toluenesulfonic acid were added and the whole was heated under reflux for 4 hours. The reaction products were analyzed by gas chromatography to reveal that aimed 1,1,1-tribromo-4-methyl-3-pentene-2-ol was formed. Conversion was 80% and selectivity was 92%. The reaction products were diluted with diethyl ether, decolorized by treatment with active carbon and subjected to reduced pressure distillation to distill out low boiling point matters. Thus resulting crystals were recrystallized from petroleum ether to obtain 3.2 parts of 1,1,1-tribromo-4-methyl-3-pentene-2-ol having the same properties as in Referential Example 19.

REFERENTIAL EXAMPLES 22 − 26

In the isomerization reaction of 1,1,1-trichloro-4-methyl-4-pentene-2-ol into 1,1,1-trichloro-4-methyl-3-pentene-2-ol, differences in conversions and selectivities to 1,1,1-trichloro-4-methyl-3-pentene-2-ol according to reaction conditions were determined by the analysis of gas chromatography. The results are shown in Table 4. Amberlyst-15 is a strongly acidic cation exchange MR-H resin (a product of Organo Co., Ltd.), and concentrations of sulfuric acid and phosphoric acid were 95% and 85%, respectively.

Table 4

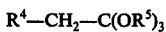
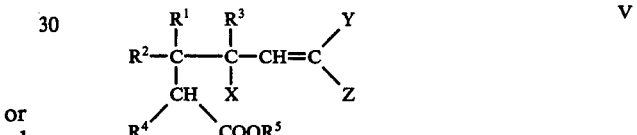

| Referential Examples | (parts) | Solvent (parts) | Acid Catalyst (parts) | Reaction temp. (° C.) | Reaction time (hr.) | Conversion (%) | Selectivity to [product] (%) |
|---|---|---|---|---|---|---|---|
| 22 | 5.0 | Benzene 25 | p-Toluene-sulfonic acid 0.08 | Reflux | 15 | 85 | 95 |
| 23 | 9.0 | n-Hexane 30 | Amberlyst-15 0.05 | Reflux | 15 | 78 | 90 |
| 24 | 5.0 | Toluene 25 | Sulfuric Acid 0.13 | Reflux | 7 | 80 | 72 |
| 25 | 5.0 | Toluene 25 | Phosphoric acid 0.16 | Reflux | 10 | 81 | 76 |
| 26 | 5.0 | None | p-Toluene-sulfonic acid 0.005 | 115 | 6 | 87 | 80 |

What we claim is:

1. A process for the preparation of a substituted cyclopropane-carboxylic ester of the formula

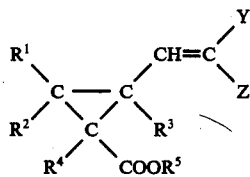

wherein $R^1$, $R^2$, $R^3$ and $R^4$, which may be the same or different, each represents a hydrogen atom, an alkyl group having up to 15 carbon atoms, a cycloalkyl group having up to 8 carbon atoms, an alkenyl group having up to 15 carbon atoms, a cycloalkenyl group having up to 8 carbon atoms, an alkynyl group having up to 15 carbon atoms, an aryl group having up to 8 carbon atoms or am aralkyl group having up to 10 carbon atoms or $R^1$ and $R^2$ or $R^1$ and $R^3$ together with the carbon atoms to which they are attached form a ring; $R^5$ represents an alkyl group having up to 15 carbon atoms, a cycloalkyl group having up to 8 carbon atoms, an alkenyl group having up to 15 carbon atoms, a cycloalkenyl group having up to 8 carbon atoms, an aralkyl group having up to 10 carbon atoms or a hydrocarbon group containing a hetero atom selected from the group consisting of nitrogen, phosphorus, sulfur and oxygen; and Y and Z, which may be the same or different, each represents a hydrogen atom or a halogen atom selected from the group consisting of F, Cl, Br and I, which process comprises (i) reacting at a temperature of from 100° C to 200° C, a 1-halogen-3-alkene-2-ol of the formula

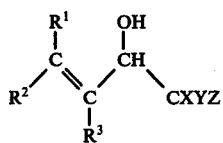

wherein $R^1$, $R^2$, $R^3$, Y and Z are as defined above, and X is a halogen atom selected from the group consisting of F, Cl, Br and I, with an ortho-carboxylic ester of the formula $$R^4-CH_2-C(OR^5)_3 \qquad III$$

wherein $R^4$ and $R^5$ are as defined above, the three groups $R^5$ being the same or different, to produce a γ-halogeno-δ-unsaturated-carboxylic acid ester of the formula $$R^2-\underset{\underset{R^4}{|}}{\overset{\overset{R^1}{|}}{C}}-\underset{\underset{COOR^5}{|}}{\overset{\overset{R^3}{|}}{C}}-CH=C\underset{Z}{\overset{Y}{\diagup}} \qquad V$$

wherein $R^1$, $R^2$, $R^3$, $R^4$, $R^5$, X, Y and Z are as defined above, and (ii) treating said compound of formula V with a basic substance at a temperature of from about −80° C to about 100° C to produce said compound of formula I'.

2. A process according to claim 1 wherein the 1-halogeno-3-alkene-2-ol of formula [II] is selected from the group consisting of
1,1,1-trichloro-4-methyl-3-penten-2-ol,
1,1,1-tribromo-4-methyl-3-penten-2-ol,
1-chloro-1,1-dibromo-4-methyl-3-penten-2-ol,
1-bromo-1,1-dichloro-4-methyl-3-penten-2-ol,
1,1-dichloro-4-methyl-3-penten-2-ol,
1,1-dibromo-4-methyl-3-penten-2-ol,
1,1,1-trichloro-4-methyl-3-hepten-2-ol,
1,1,1-tribromo-4-methyl-3-hepten-2-ol,
1,1-dichloro-4-methyl-3-hepten-2-ol,
1,1-dibromo-4-methyl-3-hepten-2-ol,
1,1,1-trichloro-4,6,6-trimethyl-3-hepten-2-ol,
1,1,1-tribromo-4,6,6-trimethyl-3-hepten-2-ol,
1,1,1-trichloro-4-ethyl-3-hexen-2-ol,
1,1,1-tribromo-4-ethyl-3-hexen-2-ol,
1,1,1-trichloro-4-methyl-3-hexen-2-ol,
1,1,1-tribromo-4-methyl-3-hexen-2-ol,
1,1,1-trichloro-3-hepten-2-ol
and
1,1,1-tribromo-3-hepten-2-ol.

3. A process according to claim 1 wherein the 1-halogeno-3-alkene-2-ol of formula [II] is 1,1,1-trichloro-4-methyl-3-penten-2-ol.

4. A process according to claim 1 wherein the 1-halogeno-3-alkene-2-ol of general [II] is 1,1,1-tribromo-4-methyl-3-penten-2-ol.

5. A process according to claim 1 wherein the 1-halogeno-3-alkene-2-ol of formula II is prepared by reacting an unsaturated compound of the formula

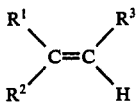   VI wherein R¹, R² and R³ are as defined in claim 1 with a halogenoacetaldehyde of the formula

VII wherein X, Y and Z are as defined in claim 34, in the presence of an acid catalyst to produce a 1-halogeno-4-alkene-2-ol, and heating said last-mentioned compound at a temperature of from 60° C to 250° C to produce the isomeric compound of formula II.

6. A process according to claim 5 wherein the unsaturated compound of formula VI is selected from the group consisting of propene, isobutene, 2-methyl-1-butene diisobutene, 1-pentene, 2-ethyl-1-butene and 2-methyl-1-pentene and the halogenoacetaldehyde of formula VII is selected from the group consisting of trichloroacetaldehyde, tribromoacetaldehyde, dichloroacetaldehyde, dibromoacetaldehyde, monochloroacetaldehyde dichlorobromoacetaldehyde, dibromochloroacetaldehyde and monobromoacetaldehyde.

7. A process according to claim 5 wherein the 1-halogeno-3-alkene-2ol of formula II is 1,1,1-trichloro-4-methyl-3-penten-2-ol, the unsaturated compound of formula VI is isobutene, the halogenoacetaldehyde of formula VII is trichloroacetaldehyde and the 1-halogeno-4-alkene-2-ol is 1,1,1-trichloro-4-methyl-4-penten-2-ol.

8. A process according to claim 5 wherein the 1-halogeno-3-alkene-2-ol of formula II is 1,1,1-tribromo-4-methyl-3-penten-2-ol, the unsaturated compound of formula VI is isobutene, the halogeno acetaldehyde of formula VII is tribromoacetaldehyde and the 1-halogeno-4-alkene-2-ol is 1,1,1-tribromo-4-methyl-4-penten-2-ol.

9. A process according to claim 1, wherein the reaction of the 1-halogeno-3-alkene-2-ol with the orthocarboxylic ester is carried out in the presence of an acid catalyst.

10. A process according to claim 9, wherein said acid catalyst is selected from the group consisting of a lower fatty acid, an aromatic carboxylic acid, a phenol, a sulfonic acid, a mineral acid and a Lewis acid.

11. A process according to claim 1 wherein said basic substance is selected from the group consisting of an alkali metal hydroxide, an alkaline earth metal hydroxide, an alkali metal alcoholate, a nitrogen-containing organic base, an organic lithium compound, an alkali metal hydride, an alkali metal amide and an alkali metal.

12. A process for the preparation of a substituted cyclopropane-carboxylic ester of the formula

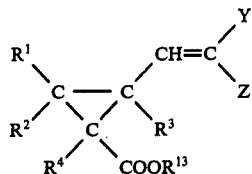   I wherein R¹, R², R³ and R⁴, which may be the same or different, each represents a hydrogen atom, an alkyl group having up to 15 carbon atoms, a cycloalkyl group having up to 8 carbon atoms, an alkenyl group having up to 15 carbon atoms, a cycloalkenyl group having up to 8 carbon atoms, an alkynyl group having up to 15 carbon atoms, an aryl group having up to 8 carbon atoms or an aralkyl group having up to 10 carbon atoms or R¹ and R² or R¹ and R³ together with the carbon atoms to which they are attached form a ring; R¹³ is a group of the formula

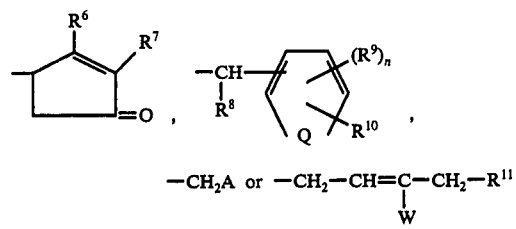

wherein R⁶ is a hydrogen atom or a methyl group; R⁷ is an alkenyl, alkadienyl or alkynyl group having up to 6 carbon atoms or a benzyl group; R⁸ is a hydrogen atom, an ethynyl group or a cyano group; R⁹ is a hydrogen atom, a halogen atom or an alkyl group having up to 5 carbon atoms; R¹⁰ is a halogen atom, an alkyl, alkenyl or alkynyl group having up to 6 carbon atoms, or a benzyl, thenyl, furylmethyl, phenoxy or phenylthio group, or R⁹ and R¹⁰ together form a polymethylene chain or such a chain interrupted by an oxygen or sulfur atom; Q is an oxygen or sulfur atom or a group —CH=CH—; $n$ is an integer of 1 or 2; A is an o-, m- or p-phenoxyphenyl group, a phthalimido group, a thiophthalimido group, a di- or tetra-hydrophthalimido group or a dialkylmaleimido group; R¹¹ is a phenyl group, a thienyl group or a furyl group; and W is a hydrogen atom, a methyl group, an alkoxy group, a cyano group or a halogen atom; and Y and Z, which may be the same or different, each represents a hydrogen atom or a halogen atom selected from the group consisting of F, Cl, Br and I, which process comprises (i) reacting at a temperature of from 100° C to 200° C, a 1-halogeno-3-alkene-2-ol of the formula

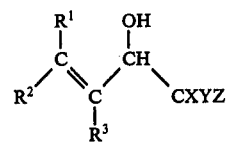   II wherein R¹, R², R³, Y and Z are as defined above, and X is a halogen atom selected from the group consisting of F, Cl, Br and I, with an ortho-carboxylic ester represented by the formula

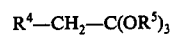   III wherein $R^4$ is as defined above and $R^5$ is an alkyl group having up to 15 carbon atoms, a cycloalkyl group having up to 8 carbon atoms, an alkenyl group having up to 15 carbon atoms, a cycloalkenyl group having up to 8 carbon atoms, an aralkyl group having up to 10 carbon atoms or a hydrocarbon group containing a hetero atom selected from the group consisting of nitrogen, phosphorus, sulfur and oxygen, the three groups $R^5$ being the same or different, to produce a γ-halogeno-δ-unsaturated-carboxylic acid ester of the formula

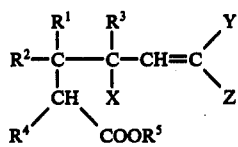  V wherein $R^1$, $R^2$, $R^3$, $R^4$, $R^5$, X, Y and Z are as defined above, (ii) reacting said γ-halogeno-δ-unsaturated-carboxylic acid ester of formula V with a basic substance at a temperature of from about −80° C to about 100° C to produce a substituted cyclopropanecarboxylic ester of the formula

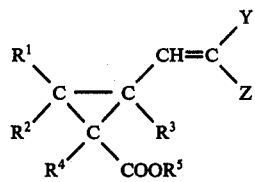  I' wherein $R^1$, $R^2$, $R^3$, $R^4$, $R^5$, Y and Z are as defined above, and (iii) contacting said ester of the formula I' with an alcohol of the formula $R^{13}OH$  VIII wherein $R^{13}$ is as defined above, to produce said compound of formula I by ester exchange.

13. A process according to claim 1, wherein the 1-halogeno-3-alkene-2-ol of general formula [II] is prepared by isomerizing a 1-halogeno-4-alkene-2-ol.

14. A process according to claim 13, wherein the 1-halogeno-3-alkene-2-ol of formula II is 1,1,1-trichloro-3-methyl-3-pentene-2-ol and the 1-halogeno-4-alkene-2-ol is 1,1,1-trichloro-3-methyl-4-pentene-2-ol.

15. A process according to claim 13, wherein the 1-halogeno-3-alkene-2-ol of formula II is 1,1,1-tribromo-3-methyl-3-pentene-2-ol and the 1-halogeno-4-alkene-2-ol, is 1,1,1-tribromo-3-methyl-4-pentene-2-ol.

* * * * *

UNITED STATES PATENT AND TRADEMARK OFFICE
CERTIFICATE OF CORRECTION

PATENT NO. : 4,113,968

DATED : September 12, 1978

INVENTOR(S) : Fumio Mori, Yoshiaki Omura, Takashi Nishida, and Kazuo Itoi.

It is certified that error appears in the above—identified patent and that said Letters Patent are hereby corrected as shown below:

In Claim 1, line 19, should read -- bon group containing a halogen atom or a hetero atom selected from the --;

In Claim 12, line 51, should read -- atoms or a hydrocarbon group containing a halogen atom or a hetero atom --.

Signed and Sealed this

Twenty-seventh Day of February 1979

[SEAL]

Attest:

RUTH C. MASON
Attesting Officer

DONALD W. BANNER
Commissioner of Patents and Trademarks